United States Patent [19]

Cohan et al.

[11] Patent Number: 5,563,143
[45] Date of Patent: Oct. 8, 1996

[54] CATECHOL DIETHER COMPOUNDS AS INHIBITORS OF TNF RELEASE

[75] Inventors: Victoria L. Cohan, Groton; Allen J. Duplantier, Ledyard, both of Conn.

[73] Assignee: Pfizer Inc., New York, N.Y.

[21] Appl. No.: 310,171

[22] Filed: Sep. 21, 1994

[51] Int. Cl.⁶ .................................................. A61N 43/54
[52] U.S. Cl. ............................................................ 514/256
[58] Field of Search ................................................ 514/216

[56] References Cited

U.S. PATENT DOCUMENTS 4,971,959   11/1990   Hawkins .............................. 514/150

FOREIGN PATENT DOCUMENTS

| 401903 | 12/1990 | European Pat. Off. ...... A61K 31/165 |
| 411754 | 2/1991 | European Pat. Off. ....... A61K 31/44 |
| 9107178 | 5/1991 | WIPO .......................... A61K 31/505 |
| 9115451 | 10/1991 | WIPO .......................... C07C 49/753 |
| 9207567 | 5/1992 | WIPO .......................... A61K 31/535 |
| 9219594 | 11/1992 | WIPO .......................... C07D 207/26 |
| 9410118 | 5/1994 | WIPO .......................... C07C 43/235 |
| 9412461 | 6/1994 | WIPO . |

OTHER PUBLICATIONS

Pohlman et al., J. of Immun., 136(12), (1986), p. 4548.
Strieter et al., Science, 243, p. 1467, (1989).
Brennan et al., The Lancet, Jul. 29, 1989, p. 244.
Farahat et al., Ann., Rheum. Dis., 52, (1993), p. 870.
Spooner et al., Clinical Immunology and Immunopathology, 62(1), S11, (1992).
W. Fiers, FEBS, 285(2), p. 199, (1991).

*Primary Examiner*—Paul J. Killos
*Attorney, Agent, or Firm*—P. C. Richardson; Gregg C. Benson; John D. Conway

[57] ABSTRACT

This invention relates to catechol diether compounds which are inhibitors of tumor necrosis factor (TNF). The catechol diether compounds are useful as inhibitors of TNF per se and in the treatment or alleviation of inflammatory conditions or disease, including but not limited to rheumatoid arthritis, osteoarthritis, asthma, bronchitis, chronic obstructive airways disease, psoriasis, allergic rhinitis, dermatitis and inflammatory bowel disease, sepsis, septic shock, tuberculosis, graft versus host disease and cachexia associated with AIDS or cancer. This invention also relates to pharmaceutical compositions useful therefor.

9 Claims, No Drawings

CATECHOL DIETHER COMPOUNDS AS INHIBITORS OF TNF RELEASE

BACKGROUND OF THE INVENTION

This invention relates to a method of inhibiting production of TNF (tumor necrosis factor) in a mammal in need thereof which method comprises administering to said mammal an effective amount of a compound of the formula (I) (shown below) or a pharmaceutically acceptable salt thereof, which, as such are also useful in the treatment or alleviation of inflammatory conditions or disease, including but not limited to rheumatoid arthritis, osteoarthritis, asthma, bronchitis, chronic obstructive airways disease, psoriasis, allergic rhinitis, dermatitis and inflammatory bowel disease, sepsis, septic shock, tuberculosis, multiple sclerosis and other autoimmune diseases, graft versus host disease and cachexia associated with AIDS or cancer; and this invention also relates to pharmaceutical compositions useful therefor.

TNF is produced by monocytes/macrophages and has a variety of biological activities relevant to the pathogenesis of rheumatoid arthritis (RA) and osteoarthritis (OA). Firstly, TNF can promote the accumulation of all leukocyte types by stimulating the endothelium to express adhesion molecules (T. H. Pohlman et al., *J. Immunol*, 136, pp. 4548–4553, 1986) and to release secondary chemotactic cytokines such as interleukin 8 (R. M. Strieter et al., *Science*, 243, pp. 1467–1469, 1989). Secondly, TNF can stimulate cells within the joint to synthesize and express the inducible cyclooxygenase enzyme (COX 2) and the inducible NO synthase. The products of these enzymes, prostaglandins and NO, are important mediators of pain and inflammation. Thirdly, and perhaps most importantly, TNF, like IL-1, can activate chondrocytes to degrade their own extracellular matrix and suppress synthesis of cartilage matrix components leading to cartilage destruction. In addition to these effects, TNF plays a pivotal role in the regulation of the production of other cytokines. This has been demonstrated in cultures of dissociated RA synovial cells where blocking the activity of TNF can inhibit the secretion of IL-1 (F. M. Brennan et al., *Lancet*, 2, pp. 244–247, 1989). Thus, blocking TNF production should prevent the synthesis of other downstream cytokines such as IL-1. Finally, TNF has been immunolocalised in both RA and OA synovial membranes (M. N. Farahat et al., *Ann. Rheum. Dis.*, 52, pp. 870–875, 1993).

TNF is recognized to be involved in many infectious and auto-immune diseases (W. Fiers, *FEBS Letters*, 1991, 285, p. 199). Furthermore, it has been shown that TNF is the prime mediator of the inflammatory response seen in sepsis and septic shock (C. E. Spooner et al., *Clinical Immunology and Immunopathology*, 1992, 62, p. S11).

The compounds utilized in the present invention are disclosed and claimed in co-pending U.S. application Ser. No. 08/157,248 filed Nov. 26, 1993, Ser. No. 08/142,328 filed Nov. 26, 1993 abd and Ser. No. 08/157,241 filed Nov. 26, 1993 abd, all of which are assigned to the assignee hereof, wherein said compounds are disclosed as having phosphodiesterase type IV (PDE$_{IV}$) inhibiting activity. The teachings thereof are incorporated herein by reference.

SUMMARY OF THE INVENTION

This invention is concerned with a method of inhibiting production of tumor necrosis factor (TNF) in a mammal in need thereof and/or a method of treating or alleviating inflammatory conditions or disease, including but not limited to rheumatoid arthritis, osteoarthritis, asthma, bronchitis, chronic obstructive airways disease, psoriasis, allergic rhinitis, dermatitis and inflammatory bowel disease, sepsis, septic shock, tuberculosis, multiple sclerosis and other autoimmune diseases, graft versus host disease and cachexia associated with AIDS or cancer which method comprises administering to said mammal an effective amount of a compound selected from the group consisting of compounds of the formula (I)

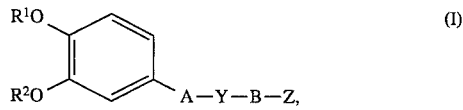

the racemic-diastereomeric mixtures and optical isomers of said compounds and the pharmaceutically acceptable salts thereof wherein $R^1$ is selected from the group consisting of methyl, ethyl, difluoromethyl and trifluoromethyl;

$R^2$ is selected from the group consisting of ($C_1$-$C_6$)alkyl, alkoxyalkyl having 3 to 7 carbons in the alkoxy portion and 2 to 4 carbons in the alkyl portion, phenoxyalkyl having 2 to 6 carbons in the alkyl portion, ($C_3$-$C_7$)cycloalkyl, ($C_6$-$C_9$)polycycloalkyl, phenylalkyl having 1 to 8 carbons in the alkyl portion, phenylaminoalkyl having 2 to 6 carbons in the alkyl portion and the amino may be optionally substituted with ($C_1$-$C_4$) alkyl and indanyl, where the alkyl portion of said alkyl, phenoxyalkyl, cycloalkyl, polycycloalkyl, phenylalkyl and indanyl may optionally be substituted with one or more fluorine atoms, —OH or ($C_1$-$C_4$)alkoxy, and the aryl portion of said phenylalkyl, phenoxyalkyl and indanyl may optionally be substituted with ($C_1$-$C_4$)alkyl, ($C_1$-$C_4$)alkoxy or halogen;

A and B are independently selected from the group consisting of a covalent bond, optionally substituted ($C_1$-$C_5$)alkylene, optionally substituted ($C_2$-$C_5$)alkenyl and optionally substituted phenylene, where said optionally substituted alkylene may be monosubstituted and each substituent is selected from the group consisting of oxo, ($C_1$-$C_4$)alkoxy, $CO_2R_6$ and hydroxy, said optionally substituted alkenyl may be monosubstituted with ($C_1$-$C_4$)alkoxy or $CO_2R^6$, and said optionally substituted phenylene may be monosubstituted with ($C_1$-$C_4$)alkoxy, $CO_2R^6$ or hydroxy, wherein $R^6$ is hydrogen or ($C_1$-$C_4$)alkyl;

Y is selected from the group consisting of a covalent bond, O, $NR^6$ and S wherein $R^6$ is as defined above;

Z is selected from the group consisting of

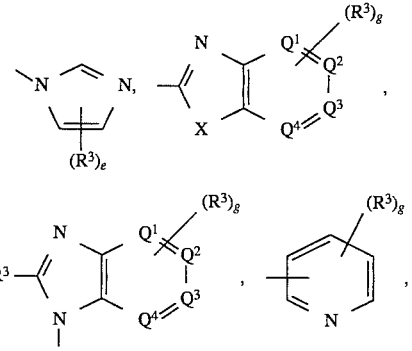

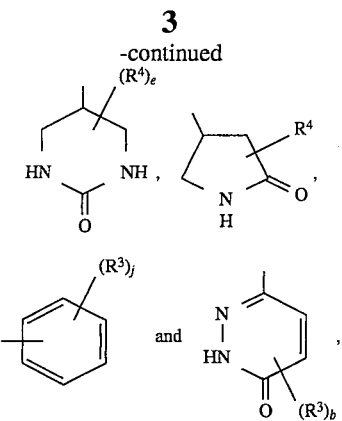

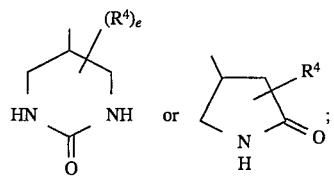

where $Q^1$, $Q^2$, $Q^3$, and $Q^4$ are independently N, CH or, when also bonded to B, C and
provided that at least two of $Q^1$, $Q^2$, $Q^3$, and $Q^4$ are not N;

X is selected from the group consisting of $NR^4$ and S;

e is an integer from 1 to 3;

g is an integer from 1 to 4;

j is an integer from 1 to 5;

each $R^3$ is independently selected from the group consisting of hydrogen, halogen, $CF_3$, $(C_1\text{-}C_6)$alkyl, $CH(R^7)CO_2R^4$, $(C_1\text{-}C_6)$alkoxy, $CO_2R^4$, $CONR^4R^5$, CONHOH, $CH_2NR^4R^5$, $NR^4R^5$, nitro, hydroxy, CN, $SO_3H$, phenylalkyl having 1 to 4 carbons in the alkyl portion, $SO_2NR^4R^5$, $N(SO_2R^8)_2$ and $NHSO_2R^8$, where $R^4$ for each occurrence is independently selected from the group consisting of hydrogen, $(C_1\text{-}C_6)$alkyl, phenyl optionally substituted with $(C_1\text{-}C_4)$alkyl or halogen, $CH(R^7)CO_2R^6$, $(C_3\text{-}C_7)$cycloalkyl, phenylalkyl having 1 to 4 carbons in the alkyl portion and dialkylaminoalkyl having a total of 5 carbons in the dialkylamino portion and having 2 to 5 carbons in the alkyl portion where $R^6$ is as defined above, $R^5$ for each occurrence is independently selected from the group consisting of hydrogen, $(C_1\text{-}C_6)$alkyl, $(C_3\text{-}C_7)$cycloalkyl, phenylalkyl having 1 to 4 carbons in the alkyl portion, phenyl, pyridyl, pyrimidyl, thiazolyl and oxazolyl, or $R^4$ and $R^5$ are taken together with the nitrogen to which they are attached and form an optionally substituted saturated or unsaturated 5- or 6-membered ring, a saturated or unsaturated 6-membered heterocyclic ring containing two heteroatoms, or a quinoline ring optionally substituted with fluoro, where said optionally substituted saturated or unsaturated 5- or 6-membered ring may be mono- or di-substituted and each substituent is independently selected from the group consisting of alkyl having 1 to 4 carbons, $CO_2R^7$ wherein $R^7$ is as defined below, $CONH_2$, $CON(CH_3)_2$, oxo, hydroxy, $NH_2$ and $N(CH_3)_2$, and said saturated or unsaturated 6-membered heterocyclic ring containing two heteroatoms has the second heteroatom selected from the group consisting of O, S, NH, $NCH_3$, $NCOCH_3$ and $NCH_2Ph$;

$R^7$ for each occurrence is independently selected from the group consisting of hydrogen and $(C_1\text{-}C_4)$alkyl;

and $R^8$ is selected from the group consisting of $(C_1\text{-}C_6)$alkyl, $(C_3\text{-}C_7)$cycloalkyl, phenyl and phenylalkyl having 1 to 4 carbons in the alkyl portion; with the proviso that:

when $R^1$ is methyl or ethyl; $R^2$ is $(C_7\text{-}C_9)$polycycloalkyl or indanyl; A, B and Y are covalent bonds; X is N; and $R^3$ is hydrogen;

then Z is not

when the compound of formula I is

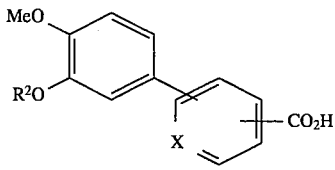

wherein X is CH or N and $R^2$ is as defined above for formula I, the $CO_2H$ can only be in the para position relative to the bond to the catechol moiety;

when the compound of formula I is

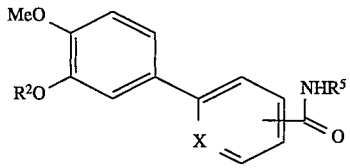

wherein X is CH or N and $R^2$ and $R^5$ are as defined above for formula I, the amide can only be in the para or meta position; and the compound of formula I cannot be trans-1-[4-[2-[3-(cyclopentyloxy)-4-methoxy-phenyl]-ethenylphenyl]-2-methyl-1H-imidazo [4,5-c]pyridine.

This invention is further directed to a method of treating or alleviating inflammatory conditions or disease, sepsis, septic shock, tuberculosis, multiple sclerosis and other autoimmune diseases, graft versus host disease or cachexia associated with AIDS or cancer in a mammal in need thereof which method comprises administering to said mammal an effective amount of a compound selected from the group consisting of compounds of the formula (I) as defined hereinabove. Thus in a further aspect, this invention provides a method of treating or alleviating rheumatoid arthritis, osteoarthritis, asthma, bronchitis, chronic obstructive airways disease, psoriasis, allergic rhinitis, dermatitis or inflammatory bowel disease, in a mammal in need thereof which comprises administering to said mammal an effective amount of a compound selected from the group consisting of compounds of the formula (I) as defined hereinabove.

Further still, this invention provides pharmaceutical compositions comprising a pharmaceutically acceptable diluent or carrier and a tumor necrosis factor inhibiting amount of a compound selected from the group consisting of compounds of the formula (I) as defined hereinabove.

A preferred method of inhibiting production of TNF in a mammal in need thereof comprises administering to said mammal an effective amount of a compound selected from the group consisting of compounds of the formula (I) wherein A, Y, B and Z are as defined hereinabove for formula (I); $R^1$ is methyl or difluoromethyl; and $R^2$ is $(C_3\text{-}C_7)$cycloalkyl, $(C_6\text{-}C_9)$polycycloalkyl, phenylalkyl, phenoxyalkyl or indanyl, where the alkyl portion of said alkyl, cycloalkyl, polycycloalkyl, phenylalkyl, phenoxyalkyl and indanyl may optionally be substituted with one or more fluorine atoms, —OH or $(C_1\text{-}C_4)$alkoxy, and the aryl portion of said phenylalkyl, phenoxyalkyl and indanyl may optionally be substituted with (C₁-C₄)alkyl, (C₁-C₄)alkoxy or halogen.

A more preferred method of inhibiting production of TNF in a mammal in need thereof comprises administering to said mammal an effective amount of a compound selected from the group consisting of compounds of the formula (I) wherein Z is as defined hereinabove for formula (I); A and B are independently selected from the group consisting of a covalent bond, (C₁-C₅)alkylene, (C₂-C₅)alkenyl and phenylene; Y is a covalent bond or O; R¹ is methyl or difluoromethyl; and R² is (C₃-C₇)cycloalkyl, (C₆-C₉)polycycloalkyl, phenylalkyl, phenoxyalkyl or indanyl, where the alkyl portion of said alkyl, cycloalkyl, polycycloalkyl, phenylalkyl, phenoxyalkyl and indanyl may optionally be substituted with one or more fluorine atoms, 1'OH or (C₁-C₄)alkoxy, and the aryl portion of said phenylalkyl, phenoxyalkyl and indanyl may optionally be substituted with (C₁-C₄)alkyl, (C₁-C₄)alkoxy or halogen.

An even more preferred method of inhibiting production of TNF in a mammal in need thereof comprises administering to said mammal an effective amount of a compound selected from the group consisting of compounds of the formula (I) wherein A is covalent bond, methylene or cis-ethenyl; B is a covalent bond or phenylene; Z is selected from the group consisting of

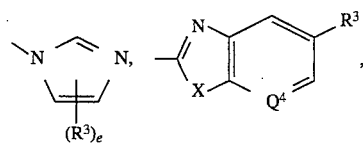

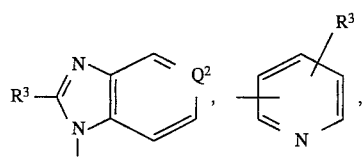

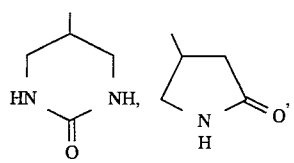

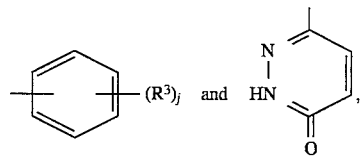

wherein R³, X and e are as defined hereinabove for formula (I); j is 1 or 2; Q⁴ is CH or N and Q² is CH or N;

Y is a covalent bond or O; R¹ is methyl or difluoromethyl; and R² is (C₃-C₇)cycloalkyl, (C₆-C₉)polycycloalkyl, phenylalkyl, phenoxyalkyl or indanyl, where the alkyl portion of said alkyl, cycloalkyl, polycycloalkyl, phenylalkyl, phenoxyalkyl and indanyl may optionally be substituted with one or more fluorine atoms, —OH or (C₁-C₄)alkoxy, and the aryl portion of said phenylalkyl, phenoxyalkyl and indanyl may optionally be substituted with (C₁-C₄)alkyl, (C₁-C₄)alkoxy or halogen.

A most preferred method of inhibiting production of TNF in a mammal in need thereof comprises administering to said mammal an effective amount of a compound selected from the group consisting of compounds of the formula (I) wherein A is covalent bond, methylene or cis-ethenyl; B is a covalent bond or phenylene; Z is selected from the group consisting of

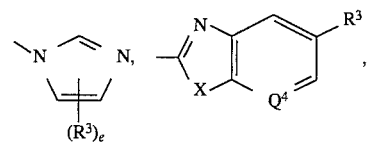

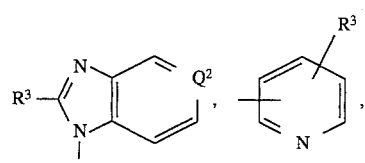

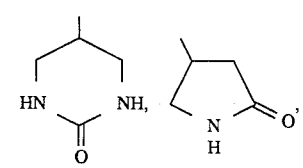

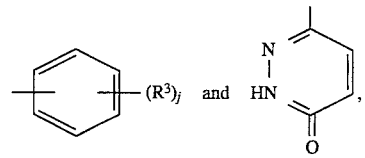

wherein X is as defined hereinabove for formula (I); j is 1 or 2; Q⁴ is CH or N; Q² is CH or N; R³ is (C₁-C₄)alkyl, CO₂H, CONH₂, nitro, NHSO₂Me, CF₃ or hydrogen; and e is 1; Y is a covalent bond or O; R¹ is methyl; and R² is cyclopentyl, norbornyl, indanyl, 1-phenylbut-3-yl, 1-phenoxyeth-2-yl, 1-phenylhex-5-yl or 1-phenylpent-4-yl.

A further most preferred method of inhibiting production of TNF in a mammal in need thereof comprises administering to said mammal an effective amount of a compound selected from the group consisting of compounds of the formula (I) wherein Z is selected from the group consisting of

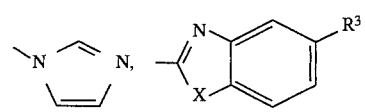

wherein R³ is H, CO₂H or CONH₂ and X is as defined hereinabove for formula (I),

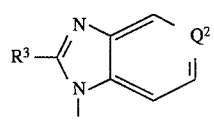

wherein R³ is (C₁-C₆)alkyl and Q² is CH or N,

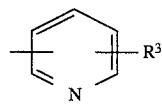

wherein $R^3$ is H, $CO_2H$ or $CONH_2$, and

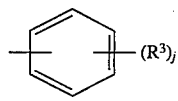

wherein $R^3$ is $(C_1-C_6)$alkyl, H, $CO_2H$, $CONH_2$ $CF_3$, $NO_2$ or $NHSO_2Me$ and j is 1 or 2; A is a covalent bond, methylene or cis-ethenyl; B is a covalent bond or phenylene; Y is a covalent bond or O; $R^1$ is methyl; and $R^2$ is cyclopentyl, norbornyl, indanyl, 1-phenylbut-3-yl, 1-phenoxyeth-2-yl, 1-phenylhex-5-yl or 1-phenyl-pent-4-yl.

As used throughout this specification and the appendant claims, the terms "alkyl" and "alkoxy" include both straight chain and branched groups; the term "halogen" includes fluoro, chloro and bromo; and the symbol "Ph" in the term "$NCH_2Ph$" means phenyl.

Those members of the substituent Z which are bicyclic are attached to the remainder of the compound of formula (I) through the ring of the Z substituent in which the bond is drawn.

As will be readily apparent to one skilled in the art, when Z is

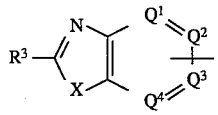

and one or more of $Q^1$, $Q^2$ $Q^3$ and $Q^4$ is N, Z cannot be bonded through one of its ring nitrogen atoms to the rest of the molecule.

DETAILED DESCRIPTION OF THE INVENTION

The compounds utilized in the methods of the present invention having the formula (I) which comprise the racemic-diastereomeric mixtures and optical isomers of said compounds and the pharmaceutically acceptable salts thereof, are readily and generally prepared by the following reaction processes.

(a) In one process certain compounds of the formula (IV) can be prepared by the Wittig synthesis, according to the following reaction scheme:

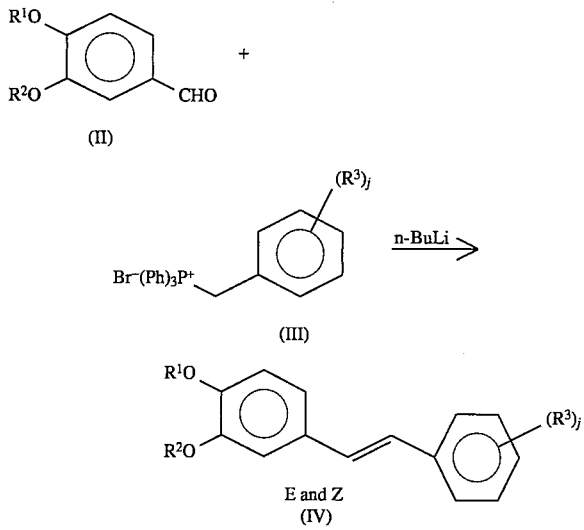

wherein $R^1$, $R^2$, $R^3$ and j are as defined above for formula (I).

In a typical procedure, approximately one equivalent of the phenylphosphonium bromide (III), dissolved or suspended in dry THF, is treated with about 1.1 equivalents of 2.5M n-BuLi in hexane. This mixture is allowed to stir at about −78° C. for about one hour. Then approximately one equivalent of the aldehyde (II), dissolved in anhydrous THF, is added to the formed yilide solution at about −78° C. After about one hour of stirring at about −78° C, the reaction mixture is allowed to warm to room temperature over about 18 hours. The reaction is worked-up by pouring it into water and extracting twice with a solvent such as ethyl acetate. The ethyl acetate is evaporated and the crude product is chromatographed on silica gel using 15% ether/hexanes as the eluant to yield the desired compound (IV). Both the cis and trans isomers of (IV) are isolated.

(b) In a further process, certain compounds of general formula (IX) can be prepared by a Mitsunobu type reaction, according to the following general reaction scheme:

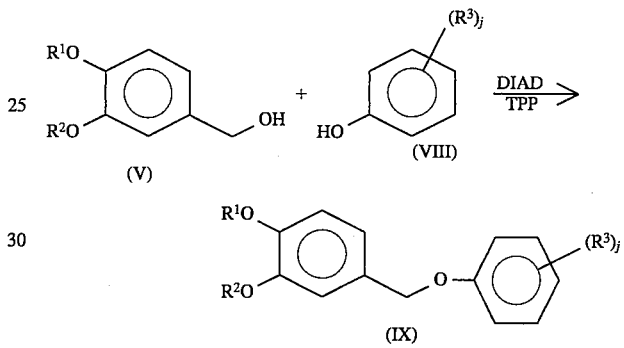

wherein $R^1$, $R^2$, $R^3$ and j are as defined above for formula (I).

In a typical procedure, about 1 to 5 equivalents, typically 1.2 equivalents, of diisopropylazodicarboxylate (DIAD) or diethylazodicarboxylate (DEAD) is added to a mixture of about one equivalent of the alcohol (V), about one equivalent of the phenol (VIII) and about 1.1 equivalents of triphenylphosphine (TPP). All of the reactants are dissolved in a dry solvent, such as tetrahydrofuran. The reaction is stirred at room temperature for about 6 to 24 hours, typically 18 hours. The solvent is evaporated and the crude oil is purified by column chromatography on silica gel to yield the compound of formula (IX).

(c) Certain compounds of the formula (XVI) may be synthesized according to the scheme shown below:

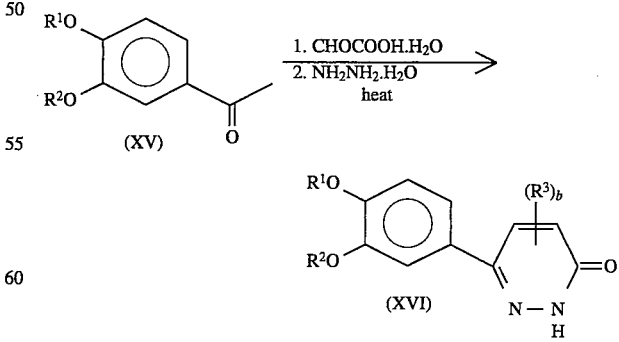

wherein $R^1$, $R^2$, $R^3$ and b are as defined above for formula (I). In a typical procedure, a ketone of the formula (XV) is heated with glyoxylic acid monohydrate at about 100° C. to 150° C., preferably about 120° C. The reaction is cooled to about 60° C. and about 2 ml of H₂O is added. About 20 to 30 drops of concentrated NH₄OH and about 1 equivalent of hydrazine monohydrate are added. The mixture is then heated at reflux for about 2 hours. It is cooled to room temperature and about 5 ml of water is added. The mixture is stirred for about 50 to 72 hours, preferably for about 60 hours. The suspension is filtered and purified by column chromatography on silica gel followed by crystallization.

(d) Certain compounds of formula (XIX) are prepared by palladium cross coupling according to the following scheme:

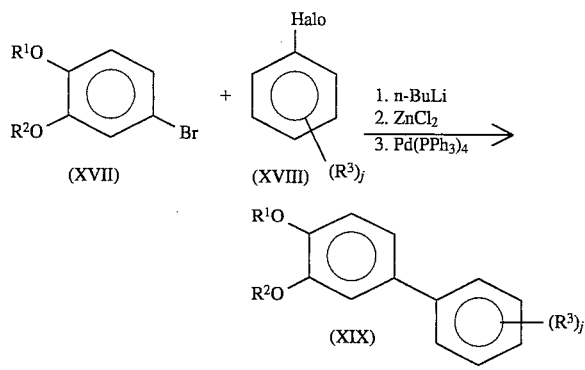

wherein $R^1$, $R^2$, $R^3$ and j are as defined above for formula (I).

A typical procedure is carried out by taking a solution of about one equivalent of the appropriate bromo compound (XVII), dissolved in dry THF, and cooling it to about −78° C. About 1.1 equivalents of a 2.5M solution of n-BuLi is added to the bromo compound and stirred for about 40 minutes at about −78° C. About 1.2 equivalents of a 1.0M solution of ZnCl₂ in ether is added and the reaction mixture allowed to warm to room temperature over about 35 minutes. A catalytic amount, about 0.05 equivalents, of tetrakis(triphenylphosphine)palladium(O) and the required halo compound (XVIII), wherein "Halo" is I, Br or Cl but preferably I or Br, are added to the reaction mixture and allowed to stir for about 12 hours. The reaction is concentrated and chromatographed on silica gel to yield the desired compound of formula (XIX).

(e) Certain compounds of formula (I) may also be synthesized by reaction of bromo compounds (XVII) with amino compounds (XXII), according to the general reaction scheme:

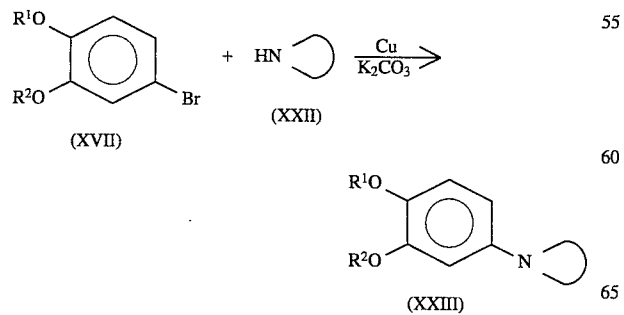

wherein $R^1$ and $R^2$ are as defined above for formula (I) and

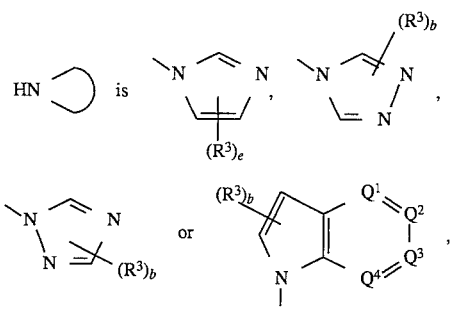

wherein $Q^1$, $Q^2$, $Q^3$, $Q^4$, $R^3$, b and e are as defined above for formula (I).

In a typical procedure, a mixture of about one equivalent of all of the reagents shown in the above scheme are heated to about 110°–150° C. for about 24 hours. The mixture is cooled to room temperature and worked-up according to standard methods well known to those skilled in the art. Chromatography on silica gel yields the desired compound of general formula (XXIII).

(f) The following procedure is employed to synthesize compounds of the formula

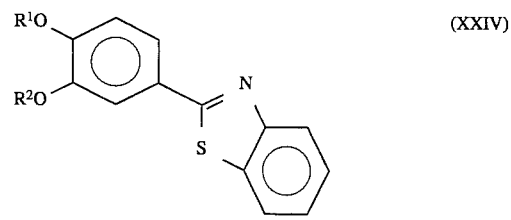

wherein $R^1$ and $R^2$ are as defined above for formula (I).

About one equivalent of an aldehyde of the formula

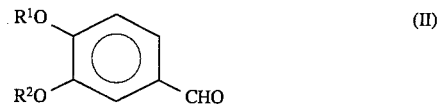

is mixed with about one equivalent of an optionally substituted 2-mercaptoaniline and heated on a steam bath for about 15 minutes. The reaction mixture is cooled and dissolved in a methanol solution of 10% FeCl₃ and stirred overnight. The reaction is diluted with H₂O and extracted with chloroform. The chloroform is evaporated and the residue is chromatographed to yield the desired benzothiazole derivatives of formula (XXIV).

(g) The following procedure is used to synthesize compounds of the formula

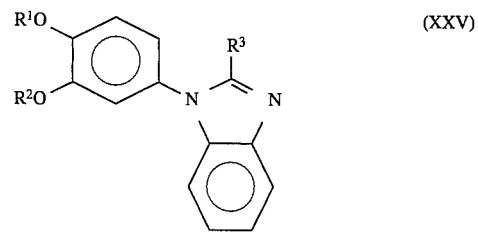

wherein $R^1$, $R^2$ and $R^3$ are as defined above for formula (I).

About one equivalent of a compound of the formula

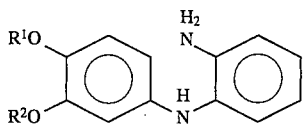 (XXVI)

is mixed with ethyl formate and approximately 25 ml of formic acid and heated at about 100° C. for about 18 hours. The solvent is evaporated and the residue chromatographed on silica gel to yield the desired benzimidazole derivatives of formula (XXV).

(h) Compounds having the general formula

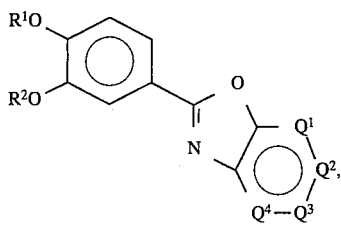 (XXVII)

wherein $R^1$, $R^2$, $Q^1$, $Q^2$, $Q^3$ and $Q^4$ are as defined above for formula (I), are synthesized by the following general method. A compound of the general formula

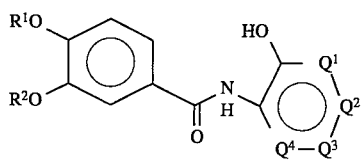 (XXVIII)

is mixed with $POCl_3$ and heated at reflux for about 24 hours. Excess $POCl_3$ is evaporated and the crude product is purified by chromatography on silica gel to yield the desired oxazolo derivatives of formula (XXVII).

(i) Compounds having the general formula N

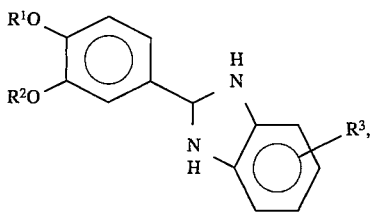 (XXXI)

wherein $R^1$, $R^2$ and $R^3$ are as defined above for formula (I), are synthesized by the following general method. A compound of the general formula (II) is mixed with an appropriate compound of the general formula

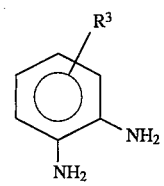 (XXXII)

and the mixture heated to about 120° C. for about 1 to 6 hours. The resulting residue is chromatographed on silica gel to yield the desired derivative of formula (XXXI).

(j) Compounds having the general formula

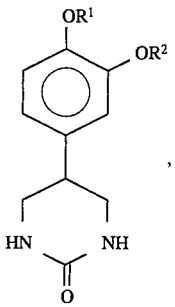 (XXXIII)

wherein $R^1$ and $R^2$ are as defined above for formula (I), are synthesized by one of the two general methods described below. The first general method is a Mitsinobu type reaction illustrated by the general scheme

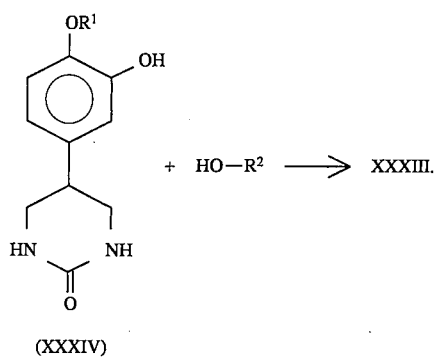

(XXXIV)

The reaction is carried out analogously to the description provided in general method (e) above.

The second general method is carried out according to the following general scheme: XXXIV+Halo-$R^2$→XXXIII, wherein "Halo" is Cl, Br or I.

A compound of general formula (XXXIV) is dissolved in anhydrous DMSO. To this mixture approximately 2.5 equivalents of anhydrous $K_2CO_3$ and the appropriate halide (Halo-$R^2$) are added. The reaction mixture is heated to about 80° C. for about 2–5 hours. After conventional work-up of the reaction mixture, the desired product is isolated by chromatography on silica gel.

As ascertained by one skilled in the art enabled by this disclosure, pharmaceutically-acceptable acid addition salts of certain compounds utilized in the present invention can be prepared which include, but are not limited to, those formed with HCl, HBr, $HNO_3$, $H_2SO_4$, $H_3PO_4$, $CH_3SO_3H$, p-$CH_3C_6H_4SO_3H$, $CH_3CO_2H$, gluconic acid, tartaric acid, maleic acid and succinic acid.

The ability of the compounds or the pharmaceutically acceptable salts thereof to inhibit TNF and, consequently, demonstrate their effectiveness for treating inflammatory conditions and diseases is shown by the following in vitro assay.

Lipopolysaccharide (LPS)-Induced TNF Release From Human Monocytes

Human Peripheral Blood Monocytes: Venous blood from healthy volunteers is collected in 25 mM EDTA. Monocytes are separated by ficoll-hypaque and washed three times in complete HBSS (Hanks Balanced Salt Solution, available from GIBCO, Grand Island, N.Y.). Cells are resuspended in a final concentration of $1.3×10^6$ cells per mL in pre-warmed RPMI (available from GIBCO, Grand Island, N.Y.) (containing 5% fetal calf serum, 2 mM glutamine, 100 units/ml penicillin/streptomycin antibiotic and 0.25 g/ml nystatin (all available from GIBCO, Grand Island, N.Y.)). Monocytes (1 mL/well) are allowed to adhere to a 24-well Primaria Plate (coated tissue culture plates, available from VWR Scientific, South Plainfield, N.J.) for 2 hours (37° C., 5% $CO_2$), after which time non-adherent cells are removed by gentle washing with RPMI.

Incubation: Compounds are dissolved in DMSO. Each compound is tested at 4 concentrations. Fresh media (HBSS) (1.0 mL) and compound (10 μL) or DMSO control is added to each well. After 1 hour at 37° C., LPS (10 ng/mL final concentration) is added to appropriate wells. Plates are incubated overnight at 37° C. At the end of the incubation period, 250 μL of each culture supernatant is removed and duplicate 10 μL samples are tested at a 1:20 dilution for TNF activity by ELISA (available from Quantikine, R&D Operations, Minneapolis, Minn.) according to the manufacturer's instructions.

TNF is determined by interpolating the average absorbance onto a standard curve. Percent inhibition is determined by the following equation: (−[pg/mL TNF experimental/pg/mL TNF DMSO control]−1)×100. $IC_{50}$ is determined by linear regression of drug concentration plotted against inhibition and interpolation of the x value at y=50 using Biostat Linear Regression Program (available from Digital, Inc., Boston, Mass.).

For administration to humans to inhibit TNF in the treatment or alleviation of inflammatory conditions or disease, including but not limited to rheumatoid arthritis, osteoarthritis, asthma, bronchitis, chronic obstructive airways disease, psoriasis, allergic rhinitis, dermatitis and inflammatory bowel disease, sepsis, septic shock, tuberculosis, graft versus host disease and cachexia associated with AIDS or cancer, oral dosages of the compounds are generally in the range of from 0.1–500 mg daily for an average adult patient (70 kg). Thus for a typical adult patient, individual tablets or capsules contain from 0.1 to 50 mg of active compound, in a suitable pharmaceutically acceptable vehicle or carrier. Tablets or capsules can be given in multiple dosages to meet the dosage requirement. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For human use, the compounds of the formula (I) can be administered alone, but will generally be administered in an admixture with a pharmaceutical diluent or carrier selected with regard to the intended route of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic. For topical administration, they are best used in the form of solutions, lotions, ointments, salves and the like.

The following examples illustrate the synthesis of certain compounds used in the present invention. The following examples combined with the synthetic methodologies described immediately above enable those skilled in the art to make the compounds used in the present invention.

EXAMPLES 1 and 2

Reaction of the appropriate aldehyde with 2-mercapto-3-aminopyridine, analogous to the following procedure yielded the following compounds. A mixture of (2 mmoles) of an appropriate aldehyde and (2.1 mmoles) 2-mercapto-3-aminopyridine hydrochloride was heated on a steam bath for about 15 minutes. The resulting thick orange oil was cooled and dissolved in 5 ml of 10% $FeCl_3$ in methanol and allowed to stir overnight. The reaction was diluted with water and extracted with $CH_2Cl_2$. The $CH_2Cl_2$ layer was dried and evaporated to give a crude product which was purified on silica gel with $CH_2Cl_2$ to give the desired product. Recrystallization was performed to further purify the desired product.

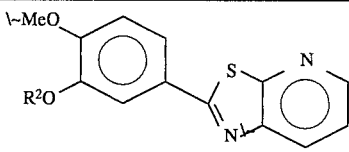

| Ex. # | $R^2$ | M.P. °C. | Calculated % C | Calculated % H | Calculated % N | Found % C | Found % H | Found % N |
|---|---|---|---|---|---|---|---|---|
| 1 | cyclopentyl | 118–120° | 66.23 | 5.56 | 8.58 | 66.41 | 5.71 | 8.42 |
| 2 | norbornyl | 110–111° | — | — | — | — | — | — |

EXAMPLE 3

6-[3-(Bicyclo [2.2.1]hept-2-yloxy)-4-methoxyphenyl]-3(2H)-pyridazinone

A mixture of 3-Exo-(±)-norbornyloxy-4-methoxyacetophenone (0.88 g, 3.38 mmol, 1.0 eq) and (0.30 g, 3.29 mmol, 0.95 eq) glyoxylic acid monohydrate was heated to about 120° C. for about 2.2 hours. The light yellow melt was cooled to about 60° C. and 2.0 ml of $H_2O$ was added. Dissolution was brought on by addition of 25 drops of concentrated $NH_4OH$. Hydrazine monohydrate (0.163 g, 3.29 mmol, 0.95 eq) was added and the reaction mixture heated to reflux for about 2 hours. The reaction mixture was cooled to room temperature, 5 ml of $H_2O$ was added to it, and the mixture stirred for about 60 hours at room temperature. The resulting suspension was filtered, washed with $H_2O$ and air dried to yield 0.87 g of a creamy yellow solid. Silica gel chromatography eluting with 5% $CH_3OH$—$CH_2Cl_2$, followed by recrystallization from isopropanol-hexane gave 0.50 g, 49%, of off-white crystals. M.P.: 188°–189° C. Elemental Analysis Calc'd for $C_{18}H_{20}N_2O_3$: Calc'd: C, 69.21; H, 6.45; N, 8.95. Found: C, 68.92; H, 6.42; N, 8.88.

EXAMPLE 4

1-[3-(Cyclopentyloxy)-4-methoxy-phenyl]-1H-imidazo[4,5-c]pyridine

A solution of 2.05 g of 1-(3-hydroxy-4-methoxyphenyl)-1H-imidazo[4,5-c]pyridine, 2.5 g of cyclopentylbromide and 665 mg of NaH in 20 ml of DMF was stirred at room temperature overnight. The reaction was poured into water and extracted with ethyl acetate, dried to give 1.4 g of crude product. Recrystallization from $CH_2Cl_2$ gave 574 mg product. M.P.: 66°–68° C.

EXAMPLE 5

Tetrahydro-5-[3-(4-phenylbutoxy)-4-methoxyphenyl]-2(1H)-pyrimidinone

Diisopropylazodicarboxylate (1.1 ml, 5.70 mmol, 1.2 eq) was added to a mixture of (1.06 g, 4.75 mmol, 1.0 eq) tetrahydro-5-(3-hydroxy-4-methoxyphenyl)-2(1H)-pyrimidinone, (1.37 g, 5.23 mmol, 1.1 eq) triphenylphosphine, and (714 mg, 4.75 mmol, 1.0 eq) 4-phenyl-1-butanol in 20 ml of anhydrous tetrahydrofuran. After heating to reflux for about 18 hours, the reaction mixture was cooled to room temperature, diluted with 350 ml ethyl acetate, washed twice with 1N NaOH, once with $H_2O$, once with brine, dried over $Na_2SO_4$, and concentrated to yield an orange solid. Silica gel chromatography eluting with 4% $CH_3OH$—$CH_2Cl_2$ yielded 527 mg of a white solid, which was recrystallized from ethyl acetate to afford 480 mg, 29%, of white needles. M.P.: 142°–143° C. Elemental Analysis Calc'd for $C_{21}H_{26}N_2O_3$: Cal'd: C, 71.17; H, 7.40; N, 7.90. Found: C, 71.12; H, 7.32; N, 7.75.

EXAMPLES 6–10

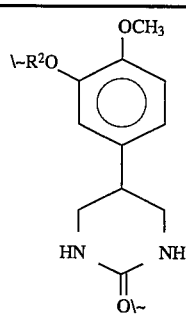

Reaction of 2(1H)-pyrimidine, tetrahydro-5-(3-hydroxy-4-methoxyphenyl)- with the appropriate alcohol of the general formula R — OH, analogous to the procedure of Example 5, yielded the following compounds:

| Ex. # | $R^2$ | M.P. °C. | Calculated (%) | | | Found (%) | | |
|---|---|---|---|---|---|---|---|---|
| | | | C | H | N | C | H | N |
| 6 | (H₃CO-norbornyl-phenyl-CH₂–) | 157–60° | 69.01 | 7.13 | 6.19 | 67.58 | 6.76 | 6.33 |
| 7 | (Ph-CH₂CH₂-CH(CH₃)–) | 152–4° | 71.17 | 7.40 | 7.90 | 71.13 | 7.42 | 7.80 |

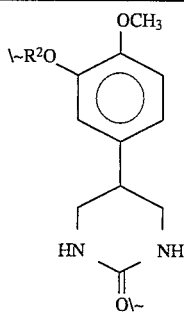

Reaction of 2(1H)-pyrimidine, tetrahydro-5-(3-hydroxy-4-methoxyphenyl)- with the appropriate alcohol of the general formula R—OH, analogous to the procedure of Example 5, yielded the following compounds:

| Ex. # | R² | M.P. °C. | Calculated (%) C | H | N | Found (%) C | H | N |
|---|---|---|---|---|---|---|---|---|
| 8 | \-Ph~~~CH₃\- | 99–101° | — | — | — | — | — | — |
| 9 | \-Ph—O~~~\- | 147–9° | — | — | — | — | — | — |
| 10 | \-Ph~~~CH₃\- | 90–2° | 72.22 | 7.91 | 7.32 | 72.20 | 7.79 | 7.27 |

EXAMPLES 11–14

Reaction of the appropriate bromocatechol with the proper halo aromatic ester of the formula X—Ar—CO—OR⁴ followed by hydrolysis analogous to the following procedure yielded the desired products. To a solution of 1.0 eq an appropriate bromocatechol in 30 ml of dry THF at about −78° C. was added 1.1 eq 2.5M n-BuLi. After stirring for about 15 minutes at about −78° C., 1.2 eq of 1.0M $ZnCl_2$ in ether was added and the mixture allowed to warm to room temperature over about 35 minutes. Tetrakis(triphenylphosphine)palladium(O) (0.05 eq) and 1.0 eq of a halo aromatic ester of the formula X—Ar—CO—OR⁴ were added to the reaction and the mixture allowed to stir at room temperature for about 2.5 hours. The reaction mixture was concentrated in vacuo, costripped with $CHCl_3$, and chromatographed on a silica gel column eluting with ethyl acetate-hexane (0–10%). Hydrolysis of the ester was accomplished as follows. A mixture of 1.0 eq the ester in 8 ml methanol and 2.0 eq of 1N NaOH was heated to reflux for about 1.5 hours. The reaction mixture was cooled to room temperature, concentrated in vacuo, poured into 100 ml $H_2O$, basified to pH 12, and washed once with ethyl acetate. The aqueous layer was acidified to pH 4 and extracted three times with ethyl acetate. The ethyl acetate extracts were combined, washed once with $H_2O$, once with brine, dried over $Na_2SO_4$, and concentrated to yield the following compounds of the general formula:

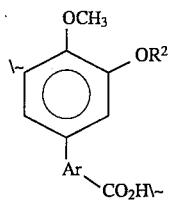

| Ex. # | R² | ArCO₂H | M.P. °C. | Calculated % C | H | N | Found % C | H | N |
|---|---|---|---|---|---|---|---|---|---|
| 11 | norbornyl | pyridyl-CO₂H | 221–3° | 70.78 | 6.24 | 4.13 | 70.60 | 6.08 | 4.02 |
| 12 | cyclopentyl | phenyl-CO₂H | 230–32° | 73.05 | 6.47 | — | 73.16 | 6.51 | — |
| 13 | norbornyl (R, −) | phenyl-CO₂H | 234–6° | 74.53 | 6.55 | — | 74.49 | 6.24 | — |
| 14 | norbornyl (R, −) | naphthyl-CO₂H | 242–4° | 77.30 | 6.23 | — | 77.28 | 6.25 | — |

EXAMPLE 15

2-[(4-Methoxy-4'-nitro[1,1'-biphenyl]-3-yl)oxy]bicyclo[2.2.1]heptane

To a stirred solution of (2 g, 6.73 mmol, 1.0 eq) (±)-1-methoxy-2-exo-nornbornyloxy- 4-bromobenzene in 50 ml of dry THF at about −78° C. was added 2.96 ml (7.40 mmol, 1.1 eq) 2.5M n-BuLi. After about 45 minutes at about −78° C., (8.07 ml, 8.07 mmol, 1.2 eq) 1.0M ZnCl₂ in ether was added and the reaction mixture allowed to warm to room temperature over about 30 minutes. Pd(PPh₃)₄ (389 mg, 0.34 mmol, 0.05 eq) and then (1.67 g, 6.73 mmol, 1.0 eq) 1-nitro-4-iodobenzene were added and the reaction mixture stirred for about 30 minutes at room temperature. The mixture was concentrated in vacuo and chromatographed on silica gel, eluting with ethyl acetate/hexane (0–8%) to afford 1.32 g, 58%, of a yellow solid. M.P.: 134°–135° C.

EXAMPLE 16

N-(3'-Bicyclo[2.2.1]hept-2-yloxy)-4'-methoxy-[1,1'-biphenyl]-4-ylmethanesulfonamide To a stirred solution of (525 mg, 1.70 mmol, 1.0 eq) 3'-(bicyclo[2.2.1]hept-2-yloxy)- 4'-methoxy[1,1'-biphenyl]-4-amino in 10 ml dry CH₂Cl₂ at about 0° C. was added 0.28 ml of triethylamine (2.03 mmol, 1.2 eq), followed by 355 mg (2.03 mmol, 1.2 eq) methanesulfonic anhydride. The mixture was stirred at about 0° C. for about 10 minutes, then at room temperature for about 1 hour, at which point an additional 200 mg (1.1 mmol, 0.7 eq) of methane sulfonic anhydride was added. After stirring an additional 30 minutes at room temperature, the reaction mixture was concentrated in vacuo, costripped twice with CHCl₃, and chromatographed on silica gel eluting with ethyl acetate-hexane (10–35%) to yield 700 mg of compound. Recrystallization from ethyl acetate/hexane afforded 650 mg, 98%, of crystals. M.P.: 151°–153° C. Elemental Analysis Calc'd for $C_{21}H_{25}NO_4S$: Calc'd: C, 65.08; H, 6.51; N, 3.61. Found: C, 64.92; H, 6.21; N, 3.53.

EXAMPLE 17

2-[3-[2-Indoxy]-4-methoxyphenyl]-1H-imidazo[4,5-b]pyridine

To a magnetically stirred solution of 3-(2-indoxy)-4-methoxybenzaldehyde (3.0 g, 11.2 mmoles) in acetone (50 ml) was added 7 ml of 2.67M solution of $Cr_2O_3$ in 50% aqueous $H_2SO_4$. This was exothermic enough to effect a mild reflux of acetone, and no external cooling was necessary. After stirring overnight at ambient temperature, 50 ml of $H_2O$ was added, and the acetone was allowed to evaporate over a steam bath. The crude product was filtered and washed with 1N HCl followed by water. Recrystallization from isopropyl ether gave 1.9 g of 3-(2-indoxy)-4-methoxybenzoic acid as off-white crystals. M.P.: 189°–191° C.

A solution of 0.50 g of 3-(2-indoxy)-4-methoxybenzoic acid in 10 ml of thionyl chloride was heated at reflux for about 1 hour. Removal of the volatiles under reduced pressure gave 3-(2-indoxy)-4-methoxybenzoyl chloride as a dull pink solid which was immediately used in the next step without purification.

To a magnetically stirred solution of 2,3-diaminopyridine (1.8 mmole) in dry pyridine (15 ml) at about 0° C. was added dropwise a solution of 3-(2-indoxy)-4-methoxybenzoyl chloride in dry THF (10 ml). After about 1 hour the mixture was warmed to ambient temperature and after about 16 hours the volatiles were removed under reduced pressure. The residue was suspended in 25 ml of water, filtered, and washed with water to give 0.59 g of a white solid. M.P.: 226°–228° C. (dec).

The above amide was suspended in 10 ml of phosphorous oxychloride and heated at reflux for about 1.5 hours, at which time the reaction mixture was homogeneous. The volatiles were removed under reduced pressure, and the residue was suspended in 25 ml of saturated sodium bicarbonate, filtered, and air-dried. Column chromatography followed by recrystallization from ethanol gave 180 mg of off-white crystals. M.P.: 206°–208° C. Elemental analysis calculated for $C_{22}H_{19}O_2N_3$: C, 73.93; H, 5.36; N, 11.76. Found: C, 73.01; H, 5.06; N, 11.76.

EXAMPLES 18–19

Reaction of the appropriate carboxylic acid with the proper amine of the general formula $NR_1R_2$, analogous to the following procedure yielded the desired compounds. A suspension of an appropriate carboxylic acid (1.38 mmoles) in dry methylene chloride was treated with excess thionyl chloride (6.93 mmoles) and a catalytic amount of anhydrous DMF (3–5 drops). The resulting clear solution was heated to reflux under nitrogen atmosphere for about 1 hour. The methylene chloride was removed in vacuo and the resulting solid residue azeotroped with an additional 15 ml of dry methylene chloride. The residue was dissolved in 15 ml of dry $CH_2Cl_2$, cooled to about 0° C. (ice bath) and dry anhydrous ammonia gas bubbled directly into the reaction mixture for approximately 5 minutes. This was followed by allowing the reaction to stir at about 0° C. for an additional hour, after which time the reaction mixture was diluted with 500 ml of ethyl acetate and 300 ml of $H_2O$. The organic layer was separated and washed with 1N HCl (2×350 ml), 2N NaOH (2×350 ml), water (1×300 ml), brine, dried over $MgSO_4$ and evaporated under reduced pressure which yielded the following compounds:

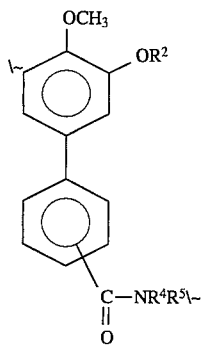

| Ex. # | $R^2$ | $R^4$ | $R^5$ | Position of Amide | M.P. °C. | Calculated % C | H | N | Found % C | H | N |
|---|---|---|---|---|---|---|---|---|---|---|---|
| 18 | (norbornyl) | H | H | Meta | 151–153° | 74.75 | 6.87 | 4.15 | 74.47 | 6.97 | 4.00 |
| 19 | (norbornyl) | H | H | Para | 245–247° | — | — | — | — | — | — |

EXAMPLE 20 cis-1-[4-[2-[3-(Cyclopentyloxy)-4-methoxyphenyl]-ethenylphenyl]-2-methyl-1H-imidazo[4,5-c]pyridine To a stirred suspension of (1.74 g, 3.13 mmol, 1.2 eq) [[3-(cyclopentyloxy)-4-methoxyphenyl]methyl]triphenylphosphonium bromide in 20 ml dry tetrahydrofuran at about −50° C. was added (1.1 ml, 2.78 mmol, 1.1 eq) of 2.5M n-BuLi. The mixture was warmed to about 0° C. over about 1 hour, cooled to about −78° C., and a solution of (600 mg, 2.53 mmol, 1.0 eq) 4-(2-methyl-1H-imidazo[4,5-c]pyridin-1-yl)benzaldehyde in 20 ml dry tetrahydrofuran was added dropwise over about 10 minutes. The reaction mixture was allowed to warm to room temperature over about 18 hours then was quenched with 10 ml saturated NH$_4$Cl solution. The mixture was poured into 200 ml of H$_2$O and extracted twice with ethyl acetate. The ethyl acetate extracts were combined, washed once with H$_2$O, once with brine, dried over MgSO$_4$, and concentrated to give 2 g of an oil. Flash chromatography eluting with 65% acetone-hexane gave 403 mg of crude product, which was recrystallized from ether-hexane to yield 305 mg, 36%, of the cis product. The cis-product M.P.: 123°–125° C. Elemental Analysis of the cis-product: Calc'd for C$_{27}$H$_{27}$N$_3$O$_2$: Calc'd: C, 76.21; H, 6.40; N, 9.87. Found: C, 76.14; H, 6.34; N, 9.71.

EAXMPLES 21–31

Additional examples, which were prepared according to the methods described and readily apparent to those skilled in the art, are shown in the following table.

| Ex. # | R$^1$ | R$^2$ | A | Y | B | Z–R$^3$ | M.P. (°C.) |
|---|---|---|---|---|---|---|---|
| 21 | CH$_3$ | indanyl | C.B. | C.B. | C.B. | phenyl-COOH | 244–247 |
| 22 | CH$_3$ | -(CH$_2$)$_n$-phenyl | C.B. | C.B. | C.B. | phenyl-COOH, CH$_3$ | 127–128 |
| 23 | CH$_3$ | norbornyl | C.B. | C.B. | C.B. | pyridyl-CONH$_2$ | 169–171 |
| 24 | CH$_3$ | -CH(CH$_3$)-(CH$_2$)$_2$-phenyl (+) | C.B. | C.B. | C.B. | phenyl-CONH$_2$ | 88–90 |
| 25 | CH$_3$ | -CH(CH$_3$)-(CH$_2$)$_2$-phenyl | C.B. | C.B. | C.B. | phenyl-CONH$_2$, CF$_3$ | 79–81 |
| 26 | CH$_3$ | norbornyl (+) | -CH$_2$- | -O- | phenyl | -(CH$_2$)$_n$-benzimidazolyl | 129–131 |
| 27 | CH$_3$ | indanyl | C.B. | C.B. | C.B. | imidazolyl | 118–119 |
| 28 | CH$_3$ | indanyl | C.B. | C.B. | C.B. | benzimidazolyl-COOH | 185–187 |

-continued

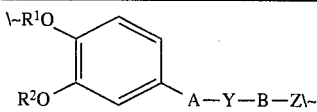

| Ex. # | R¹ | R² | A | Y | B | Z—R³ | M.P. (°C.) |
|---|---|---|---|---|---|---|---|
| 29 | CH₃ | (norbornyl) | C.B. | C.B. | C.B. | (benzimidazole-COOH, H on N) | 221–223 |
| 30 | CH₃ | (CH(CH₃)CH₂CH₂CH₂-phenyl) | C.B. | C.B. | C.B. | (CH₂-cyclic urea with =O, NH) | 131–133 |
| 31 | CH₃ | (norbornyl) | C.B. | C.B. | C.B. | (imidazo-pyridine, H on N) | 153–154 |

*C.B. = Covalent Bond

PREPARATION 1

3-(Bicyclo[2.2.1]hept-2-yloxy)-4-methoxybenzaldehyde

Diisopropylazodicarboxylate (7.8 ml, 39.5 mmol, 1.2 eq) was added neat to a 25° solution of (5.00 g, 32.9 mmol, 1.0 eq) 3-hydroxy-4-methoxybenzaldehyde (9.48 g, 36.1 mmol, 1.1 eq) triphenylphosphine, and (3.69 g, 32.9 mmol, 1.0 eq) (±)-endo-norborneol in 100 ml of anhydrous tetrahydrofuran. After refluxing for 6 hours, the reaction mixture was poured into 1 liter of H₂O and extracted twice with ethyl acetate. The ethyl acetate layers were combined and washed twice with H₂O, once with 1N NaOH, once with H₂O and once with brine and then the solution was dried over anhydrous sodium sulfate. Filtration, concentration, and drying afforded 26.1 g of crude product, which was chromatographed on a silica gel column, eluting with 20% ethyl acetate-hexane to afford 5.68 g, 70% yield, of a yellow oil. IR(cm⁻¹): 1680, 1580. NMR (CHCl₃): δ 9.82 (s, 1H), δ 4.27 (d, 1H). High resolution mass spectra (HRMS): 246.1300.

PREPARATIONS 2–8

Reaction of the appropriate vanillin with the requisite alcohol of the formula R²—OH, analogous to the procedure of Preparation 1, afforded the following compounds:

| | | | | | | Mass Spec | Analysis | | | |
|---|---|---|---|---|---|---|---|---|---|---|
| | | | | | | | Calculated (%) | | Found (%) | |
| Prep. # | R¹ | R | R² | M.P. °C. | M.W. | (M+) | C | H | C | H |
| 2 | CH₃ | —CHO | (cyclopentyl) | oil | 220.3 | 220 | — | — | — | — |
| 3 | CH₃ | —C(=O)—CH₃ | (norbornyl) sm=endo prod=exo | oil | 260.3 | 260 | 73.82 | 7.74 | 73.19 | 8.03 |

PREPARATION 4

Bis(2-methoxy-5-bromophenyl)carbonate

Dissolved (8.26 ml, 160 mmol, 2.2 eq) bromine in 10 ml of $CHCl_3$ and then added it dropwise over 10 minutes to (20.0 g, 72.9 mmol, 1.0 eq) of bis(2-methoxy-phenyl)carbonate in 60 ml of $CHCl_3$ at room temperature. Stirred for 60 minutes at room temperature, then filtered the reaction mixture, washing the precipitate three times with $CHCl_3$ and once with hexane. The precipitate was recrystallized from $CHCl_3$ to yield 20.7 g, 66% yield, of bis(2-methoxy-5-bromophenyl)carbonate as white prisms.

PREPARATION 5

5-Bromoguaiacol

A suspension of (20.7 g, 47.9 mmol, 1.0 eq) bis(2-methoxy-5-bromophenyl)carbonate in 250 ml methanol and 60 ml (120 mmol, 2.5 eq) of 2N NaOH was refluxed for 2 hours. The reaction mixture was cooled to room temperature, concentrated to a volume of ca 100 ml, and poured into 1 L of $H_2O$. The pH was adjusted to 2 using 1N HCl. The acidic mixture was transferred to a separatory funnel, and extracted three times with ether. The ether extracts were combined and washed once with $H_2O$, once with brine, and then dried over anhydrous sodium sulfate. Filtration, concentration and drying afforded 19.0 g of a white solid, which was recrystallized from petroleum ether to yield 17.63 g, 91% yield, of white prisms.

PREPARATION 6

2-(5-Bromo-2-methoxyphenoxy)bicyclo[2.2.1]heptane

Neat diethylazodicarboxylate (1.4 ml, 8.87 mmol, 1.2 eq) was added to a 25° C. solution of (1.50 g, 7.39 mmol, 1.0 eq) 5-bromoguaiacol, (2.13 g, 8.13 mmol, 1.1 eq) triphenylphosphine and (0.829 g, 7.39 mmol, 1.0 eq) of S(−)endo-norborneol in 25 ml of anhydrous tetrahydrofuran. After stirring 18 hours at room temperature under $N_2$, the reaction mixture was diluted with 350 ml of ether, washed twice with 1N NaOH, once with $H_2O$, once with brine, and then dried over anhydrous $Na_2SO_4$. Filtration, concentration and drying afforded a yellow oil which was triturated with ca 250 ml of 1:1 ether-hexane to remove triphenylphosphine oxide. The filtrate was concentrated in vacuo, and chromatographed on a silica gel column, eluting with 10% ethyl acetate-hexane, to afford 1.75 g, 80% yield, of a clear, colorless oil. Elemental Analysis: Calc'd for $C_{14}H_{17}O_2Br$: Calc'd: C, 56.57; H, 5.77%. Found: C, 56.68; H, 5.73%.

PREPARATIONS 7–13

Reaction of 5-bromoguaiacol with the requisite alcohol of the formula $R^2$—OH, analogous to the procedure of Preparation 11, afforded the following compounds:

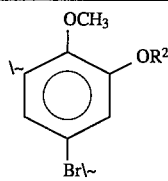

| Prep. # | $R^2$ | M.P. °C. | M.W. | Mass Spec (M+) | Calculated (%) C | Calculated (%) H | Found (%) C | Found (%) H |
|---|---|---|---|---|---|---|---|---|
| 7 | 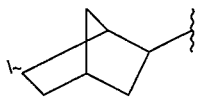 endo = sm exo = prod\~ | oil | 297.3 | 298 | — | — | — | — |
| 8 | 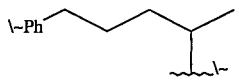 | oil | 349.3 | 350 | — | — | — | — |
| 9 |  R(+) = sm S(+) = prod\~ | oil | 297.2 | 298 | 56.57 | 5.77 | 56.74 | 5.72 |

-continued

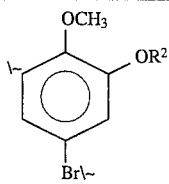

| Prep. # | R² | M.P. °C. | M.W. | Mass Spec (M+) | Calculated (%) C | Calculated (%) H | Found (%) C | Found (%) H |
|---|---|---|---|---|---|---|---|---|
| 10 | \-Ph~~~ (R(−) = sm, S(+) = prod\-) | oil | 349.29 | 349.2 | 61.89 | 6.09 | 61.18 | 6.10 |
| 11 | \-Ph~~~ (S(+) = sm, R(+) = prod\-) | oil | 349.29 | 349.2 | 61.89 | 6.09 | 59.77 | 5.66 |
| 12 | cyclopentyl | oil | 271.17 | 271.1 | 53.16 | 5.58 | 53.41 | 5.62 |
| 13 | \-Ph~~~ | oil | 335.26 | — | — | — | — | — |

*sm = starting material
prod = product

PREPARATION 14

3-Cyclopentyl-4-methoxybenzoic acid

To a stirred suspension of (5.0 g, 27 mmol, 1.0 eq) methyl vanillate, (2.5 ml, 27 mmol, 1.0 eq) cyclopentanol, and (7.4 g, 28 mmol, 1.05 eq) triphenylphosphine in 40 ml of anhydrous tetrahydrofuran was added (4.7 ml, 29.7 mmol, 1.1 eq) of diethylazodicarboxylate. The reaction mixture was stirred 18 hours at room temperature, concentrated in vacuo, and flash chromatographed on a silica gel column, eluting with 20% ethyl acetate/hexane, to yield 7.0 g, >100%, of an oil, methyl-3-methoxy-4-cyclopentyloxybenzoate.

A mixture of (7.0 g, 27 mmol, 1.0 eq) methyl-3-methoxy-4-cyclopentyloxy benzoate, 8 ml (42 mmol, 1.5 eq) 5N NaOH and 40 ml MeOH was refluxed for 3 hours. The mixture was concentrated to ca 20 ml, poured into 400 ml $H_2O$ (pH 10) and washed twice with ether. The aqueous layer was acidified to pH 1 and extracted twice with ether. The ether extracts were combined, washed once with $H_2O$, once with brine, dried over $MgSO_4$ and then concentrated to yield 6 g of a white solid. Recrystallization from ether-hexane yielded 5.60 g, 88%, of white crystals. Elemental Analysis: Calcd. for $C_{13}H_{16}O_4$: Calc'd: C, 66.09; H, 6.83. Found: C, 66.20; H, 6.64.

PREPARATION 15

2-Butyl-3-(4-hydroxyphenyl)benzimidazole

A mixture of (8.0 g, 51 mmol, 1.0 eq) 1-chloro-2-nitrobenzene and (5.54 g, 51 mmol, 1.0 eq) 4-aminophenol in 40 ml of dry dimethylsulfoxide was heated to reflux for 18 hours. The reaction mixture was cooled, poured into 400 ml of 0.1N HCl and 400 ml ethyl acetate, stirred, and filtered through celite. The filtrate layers were separated, and the aqueous layer was extracted with ethyl acetate. The ethyl acetate extracts were combined, washed twice with $H_2O$, once with brine, dried over $MgSO_4$, and concentrated to give 8 g of a dark oil. Silica gel chromatography eluting with 20% ethyl acetate/hexane gave 1.63 g, 14%, of a red solid.

A mixture of (1.6 g, 6.89 mmol, 1.0 eq) 4-N-(2-nitrophenyl)amino phenol and 800 mg of 10% Pd/C in 100 ml ethyl acetate was placed on a Parr hydrogenation apparatus and shaken under 50 psi $H_2$ for 3 hours. The mixture was filtered through celite, concentrated in vacuo, and chromatographed on a silica gel column eluting with 50% ethyl acetate/hexane to give 1.3 g, 94%, of an orange-yellow solid.

A mixture of (600 mg, 3.00 mmol, 1.0 eq) 4-N-(2-aminophenyl)amino phenol and 10 ml valeric anhydride was heated to reflux for 18 hours. The mixture was taken up in 50 ml of methanol, basified with 2N NaOH to pH 10, and stirred 1 hour at room temperature. The reaction mixture was then neutralized and extracted twice with ethyl acetate. The ethyl acetate extracts were combined, washed twice with $H_2O$, once with brine, dried over $MgSO_4$ and concentrated to give 1 g of an oil. Silica gel chromatography eluting with 2½% $CH_3OH$—$CH_2Cl_2$ gave 124 mg, 16%, solid. M.P.: 192°–194° C.

PREPARATION 16

4-[(5-Bromo-2-methoxy)phenoxy]butanoic acid ethyl ester

A mixture of 15.0 g (0.0740 mol) of 2-methoxy-4-bromophenol, 17.4 g (0.0890 mol) of ethyl 4-bromobutyrate, 20.5 g (0.148 mol) or $K_2CO_3$, and 200 ml of DMF was stirred at about 80° C. was continued for about 16 h. The combined ether extracts were washed with brine (1×300 ml), dried ($MgSO_4$), and evaporated to give 26.0 g of an orange oil. Purification by flash chromatography using an ethyl acetate-hexane (1:4) eluant gave 19.7 g (84%) of the title compound as a clear oil ($R_f$ 0.5 EtOAc-hexane, 3:7). $^1$H-NMR ($CDCl_3$) δ 1.25 (3H, t, J=7), 2.09–2.18 (2H, m), 2.51 (2H, t, J=7), 3.82 (3H, s), 4.03 (2H, t, J=7), 4.13 (2H, q, J=7), 6.72 (1H, d, J=8), 6.97–7.08 (2H, m).

What is claimed is:

1. A method of inhibiting production of TNF (tumor necrosis factor) in a mammal in need thereof which method comprises administering to said mammal an effective amount of a compound selected from the group consisting of compounds of the formula (I)

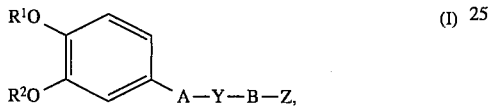
(I)

the racemic-diastereomeric mixtures and optical isomers of said compounds and the pharmaceutically acceptable salts thereof wherein $R^1$ is selected from the group consisting of methyl, ethyl, difluoromethyl and trifluoromethyl;

$R^2$ is selected from the group consisting of ($C_1$-$C_6$)alkyl, alkoxyalkyl having 3 to 7 carbons in the alkoxy portion and 2 to 4 carbons in the alkyl portion, phenoxyalkyl having 2 to 6 carbons in the alkyl portion, ($C_3$-$C_7$)cycloalkyl, ($C_6$-$C_9$)polycycloalkyl, phenylalkyl having 1 to 8 carbons in the alkyl portion, phenylaminoalkyl having 2 to 6 carbons in the alkyl portion and the amino may be optionally substituted with ($C_1$-$C_4$) alkyl and indanyl, where the alkyl portion of said alkyl, phenoxyalkyl, cycloalkyl, polycycloalkyl, phenylalkyl and indanyl may optionally be substituted with one or more fluorine atoms, —OH or ($C_1$-$C_4$)alkoxy, and the aryl portion of said phenylalkyl, phenoxyalkyl and indanyl may optionally be substituted with ($C_1$-$C_4$)alkyl, ($C_1$-$C_4$)alkoxy or halogen;

A and B are independently selected from the group consisting of a covalent bond, optionally substituted ($C_1$-$C_5$)alkylene, optionally substituted ($C_2$-$C_5$)alkenyl and optionally substituted phenylene, where said optionally substituted alkylene may be monosubstituted and each substituent is selected from the group consisting of oxo, ($C_1$-$C_4$)alkoxy, $CO_2R^6$ and hydroxy, said optionally substituted alkenyl may be monosubstituted with ($C_1$-$C_4$)alkoxy or $CO_2R^6$, and said optionally substituted phenylene may be monosubstituted with ($C_1$-$C_4$)alkoxy, ($CO_2R^6$ hydroxy, wherein $R^6$ is hydrogen or ($C_1$-$C_4$)alkyl;

Y is selected from the group consisting of a covalent bond, O, $NR^6$ and S wherein $R^6$ is as defined above;

Z is selected from the group consisting of

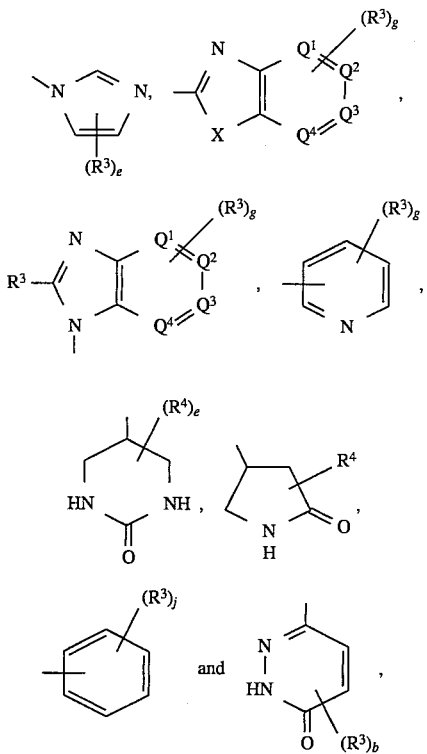

where $Q^1$, $Q^2$, $Q^3$, and $Q^4$ are independently N, CH or, when also bonded to B, C and provided that at least two of $Q^1$, $Q^2$, $Q^3$, and $Q^4$ are not N;

X is selected from the group consisting of $NR^4$ and S;

e is an integer from 1 to 3;

g is an integer from 1 to 4;

j is an integer from 1 to 5;

each $R^3$ is independently selected from the group consisting of hydrogen, halogen, $CF_3$, ($C_1$-$C_6$)alkyl, $CH(R^7)CO_2R^4$, ($C_1$-$C_6$)alkoxy, $CO_2R^4$, $CONR^4R^5$, CONHOH, $CH_2NR^4R^5$, $NR^4R^5$, nitro, hydroxy, CN, $SO_3H$, phenylalkyl having 1 to 4 carbons in the alkyl portion, $SO_2NR^4R^5$, $N(SO_2R^8)_2$ and $NHSO_2R^8$, where $R^4$ for each occurrence is independently selected from the group consisting of hydrogen, ($C_1$-$C_6$)alkyl, phenyl optionally substituted with ($C_1$-$C_4$)alkyl or halogen, $CH(R^7)CO_2R^6$, ($C_3$-$C_7$)cycloalkyl, phenylalkyl having 1 to 4 carbons in the alkyl portion and dialkylaminoalkyl having a total of 5 carbons in the dialkylamino portion and having 2 to 5 carbons in the alkyl portion where $R^6$ is as defined above, $R^5$ for each occurrence is independently selected from the group consisting of hydrogen, ($C_1$-$C_6$)alkyl, ($C_3$-$C_7$)cycloalkyl, phenylalkyl having 1 to 4 carbons in the alkyl portion, phenyl, pyridyl, pyrimidyl, thiazolyl and oxazolyl, or $R^4$ and $R^5$ are taken together with the nitrogen to which they are attached and form an optionally substituted saturated or unsaturated 5-or 6-membered ring, a saturated or unsaturated 6-membered heterocyclic ring containing two heteroatoms, or a quinoline ring optionally substituted with fluoro, where said optionally substituted saturated or unsaturated 5- or 6-membered ring may be mono-or di-substituted and each substituent is independently selected from the group consisting of alkyl having 1 to 4 carbons, $CO_2R^7$ wherein $R^7$ is as defined below, CONH$_2$, CON(CH$_3$)$_2$, oxo, hydroxy, NH$_2$ and N(CH$_3$)$_2$, and said saturated or unsaturated 6-membered heterocyclic ring containing two heteroatoms has the second heteroatom selected from the group consisting of O, S, NH, NCH$_3$, NCOCH$_3$ and NCH$_2$Ph;

R$^7$ for each occurrence is independently selected from the group consisting of hydrogen and (C$_1$-C$_4$)alkyl;

and R$^8$ is selected from the group consisting of (C$_1$-C$_6$)alkyl, (C$_3$-C$_7$)cycloalkyl, phenyl and phenylalkyl having 1 to 4 carbons in the alkyl portion;

with the proviso that:

when R$^1$ is methyl or ethyl; R$^2$ is (C$_7$-C$_9$)polycycloalkyl or indanyl; A, B and Y are covalent bonds; X is N; and R$^3$ is hydrogen;

then Z is not

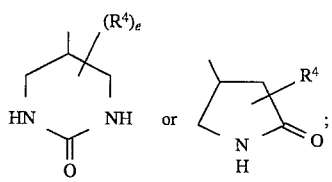

when the compound of formula I is

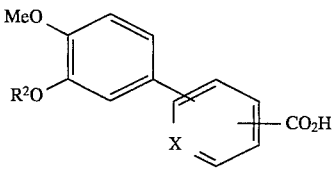

wherein X is CH or N and R$^2$ is as defined above for formula I, the CO$_2$H can only be in the para position relative to the bond to the catechol moiety;

when the compound of formula I is

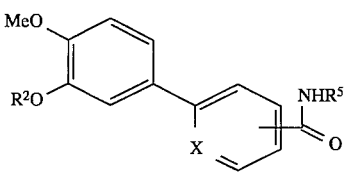

wherein X is CH or N and R$^2$ and R$^5$ are as defined above for formula I, the amide can only be in the para or meta position; and the compound of formula I cannot be trans-1-[4-[2-[3-(cyclopentyloxy)-4-methoxy-phenyl]-ethenylphenyl]-2-methyl-1H-imidazo[4,5-c]pyridine.

2. A method of inhibiting production of TNF in a mammal in need thereof according to claim 1 wherein R$^1$ is methyl or difluoromethyl; R$^2$ is (C$_3$-C$_7$)cycloalkyl, (C$_6$-C$_9$)polycycloalkyl, phenylalkyl, phenoxyalkyl or indanyl, where the alkyl portion of said alkyl, cycloalkyl, polycycloalkyl, phenylalkyl, phenoxyalkyl and indanyl may optionally be substituted with one or more fluorine atoms, —OH or (C$_1$-C$_4$)alkoxy, and the aryl portion of said phenylalkyl, phenoxyalkyl and indanyl may optionally be substituted with (C$_1$-C$_4$)alkyl, (C$_1$-C$_4$)alkoxy or halogen.

3. A method of inhibiting production of TNF in a mammal in need thereof according to claim 2 wherein A and B are independently selected from the group consisting of a covalent bond, (C$_1$-C$_5$)alkylene, (C$_2$-C$_5$)alkenyl and phenylene; and Y is a covalent bond or O.

4. A method of inhibiting production of TNF in a mammal in need thereof according to claim 3 wherein A is covalent bond, methylene or cis-ethenyl; B is a covalent bond or phenylene and Z is selected from the group consisting of

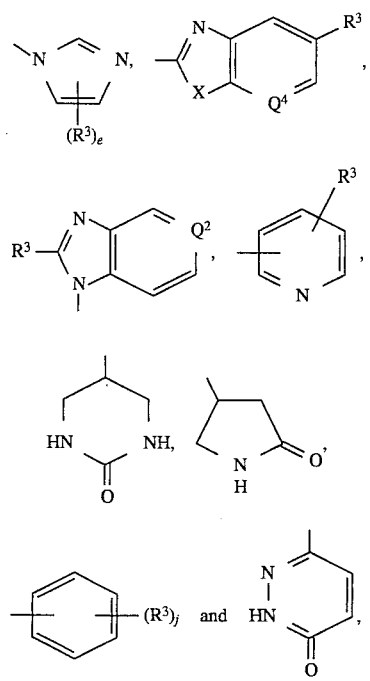

wherein j is 1 or 2; Q$^4$ is CH or N and Q$^2$ is CH or N.

5. A method of inhibiting production of TNF in a mammal in need thereof according to claim 4 wherein R$^1$ is methyl; R$^2$ is cyclopentyl, norbornyl, indanyl, 1-phenylbut- 3-yl, 1-phenoxyeth-2-yl, 1-phenylhex-5-yl or 1-phenylpent-4-yl; R$^3$ is (C$_1$-C$_4$)alkyl, CO$_2$H, CONH$_2$, nitro, NHSO$_2$Me, CF$_3$ or hydrogen; and e is 1.

6. A method of inhibiting production of TNF in a mammal in need thereof according to claim 5 wherein Z is selected from the group consisting of

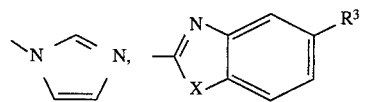

wherein R$^3$ is H, CO$_2$H or CONH$_2$,

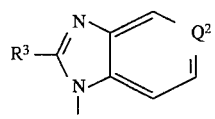

wherein $R^3$ is $(C_1-C_6)$alkyl,

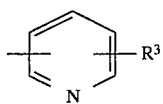

wherein $R^3$ is H, $CO_2H$ or $CONH_2$, and

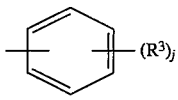

wherein $R^3$ is $(C_1-C_6)$alkyl H, $CO_2H$, $CONH_2$ $CF_3$, $NO_2$ or $NHSO_2Me$.

7. A method of treating or alleviating an inflammatory condition or disease, sepsis, septic shock, tuberculosis, multiple sclerosis and other autoimmune diseases, graft versus host disease or cachexia associated with AIDS or cancer in a mammal in need thereof which method comprises administering to said mammal an effective amount of a compound selected from the group of compounds of the formula (I)

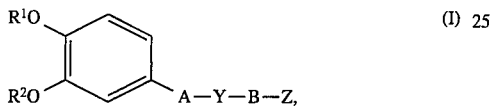
(I)

the racemic-diastereomeric mixtures and optical isomers of said compounds and the pharmaceutically acceptable salts thereof wherein $R^1$ is selected from the group consisting of methyl, ethyl, difluoromethyl and trifluoromethyl;

$R^2$ is selected from the group consisting of $(C_1-C_6)$alkyl, alkoxyalkyl having 3 to 7 carbons in the alkoxy portion and 2 to 4 carbons in the alkyl portion, phenoxyalkyl having 2 to 6 carbons in the alkyl portion, $(C_3-C_7)$cycloalkyl, $(C_6-C_9)$polycycloalkyl, phenylalkyl having 1 to 8 carbons in the alkyl portion, phenylaminoalkyl having 2 to 6 carbons in the alkyl portion and the amino may be optionally substituted with $(C_1-C_4)$ alkyl and indanyl, where the alkyl portion of said alkyl, phenoxyalkyl, cycloalkyl, polycycloalkyl, phenylalkyl and indanyl may optionally be substituted with one or more fluorine atoms, —OH or $(C_1-C_4)$alkoxy, and the aryl portion of said phenylalkyl, phenoxyalkyl and indanyl may optionally be substituted with $(C_1-C_4)$alkyl, $(C_1-C_4)$alkoxy or halogen;

A and B are independently selected from the group consisting of a covalent bond, optionally substituted $(C_1-C_5)$alkylene, optionally substituted $(C_2-C_5)$alkenyl and optionally substituted phenylene, where said optionally substituted alkylene may be monosubstituted and each substituent is selected from the group consisting of oxo, $(C_1-C_4)$alkoxy, $CO_2R^6$ and hydroxy, said optionally substituted alkenyl may be monosubstituted with $(C_1-C_4)$alkoxy or $CO_2R^6$, and said optionally substituted phenylene may be monosubstituted with $(C_1-C_4)$alkoxy, $CO_2R^6$ or hydroxy, wherein $R^6$ is hydrogen or $(C_1-C_4)$alkyl;

Y is selected from the group consisting of a covalent bond, O, $NR^6$ and S wherein $R^6$ is as defined above;

Z is selected from the group consisting of

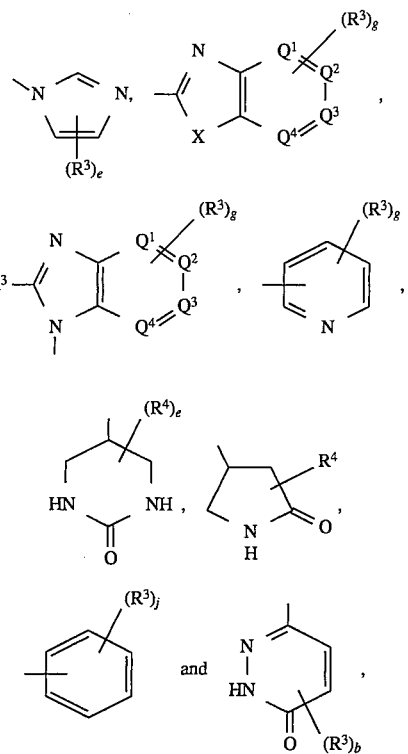

where $Q^1$, $Q^2$, $Q^3$, and $Q^4$ are independently N, CH or, when also bonded to B, C and provided that at least two of $Q^1$, $Q^2$, $Q^3$, and $Q^4$ are not N;

X is selected from the group consisting of $NR^4$ and S;

e is an integer from 1 to 3;

g is an integer from 1 to 4;

j is an integer from 1 to 5;

each $R^3$ is independently selected from the group consisting of hydrogen, halogen, $CF_3$, $(C_1-C_6)$alkyl, $CH(R^7)CO_2R^4$, $(C_1-C_6)$alkoxy, $CO_2R^4$, $CONR^4R^5$, $CONHOH$, $CH_2NR^4R^5$, $NR^4R^5$, nitro, hydroxy, CN, $SO_3H$, phenylalkyl having 1 to 4 carbons in the alkyl portion, $SO_2NR^4R^5$, $N(SO_2R^8)_2$ and $NHSO_2R^8$, where $R^4$ for each occurrence is independently selected from the group consisting of hydrogen, $(C_1-C_6)$alkyl, phenyl optionally substituted with $(C_1-C_4)$alkyl or halogen, $CH(R^7)CO_2R^6$, $(C_3-C_7)$cycloalkyl, phenylalkyl having 1 to 4 carbons in the alkyl portion and dialkylaminoalkyl having a total of 5 carbons in the dialkylamino portion and having 2 to 5 carbons in the alkyl portion where $R^6$ is as defined above, $R^5$ for each occurrence is independently selected from the group consisting of hydrogen, $(C_1-C_6)$alkyl, $(C_3-C_7)$cycloalkyl, phenylalkyl having 1 to 4 carbons in the alkyl portion, phenyl, pyridyl, pyrimidyl, thiazolyl and oxazolyl, or $R^4$ and $R^5$ are taken together with the nitrogen to which they are attached and form an optionally substituted saturated or unsaturated 5-or 6-membered ring, a saturated or unsaturated 6-membered heterocyclic ring containing two heteroatoms, or a quinoline ring optionally substituted with fluoro, where said optionally substituted saturated or unsaturated 5- or 6-membered ring may be mono-or di-substituted and each substituent is independently selected from the group consisting of alkyl having 1 to 4 carbons, $CO_2R^7$ wherein $R^7$ is as defined below, CONH$_2$, CON(CH$_3$)$_2$, oxo, hydroxy, NH$_2$ and N(CH$_3$)$_2$, and said saturated or unsaturated 6-membered heterocyclic ring containing two heteroatoms has the second heteroatom selected from the group consisting of O, S, NH, NCH$_3$, NCOCH$_3$ and NCH$_2$Ph;

R$^7$ for each occurrence is independently selected from the group consisting of hydrogen and (C$_1$-C$_4$)alkyl;

and R$^8$ is selected from the group consisting of (C$_1$-C$_6$)alkyl, (C$_3$-C$_7$)cycloalkyl, phenyl and phenylalkyl having 1 to 4 carbons in the alkyl portion;

with the proviso that:

when R$^1$ is methyl or ethyl; R$^2$ is (C$_7$-C$_9$)polycycloalkyl or indanyl; A, B and Y are covalent bonds; X is N; and R$^3$ is hydrogen;

then Z is not

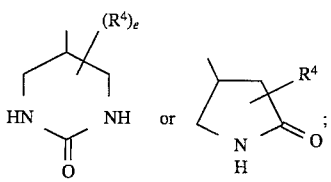

when the compound of formula I is

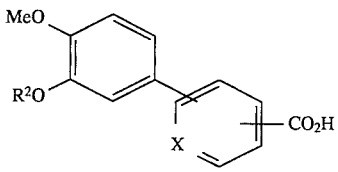

wherein X is CH or N and R$^2$ is as defined above for formula I, the CO$_2$H can only be in the para position relative to the bond to the catechol moiety;

when the compound of formula I is

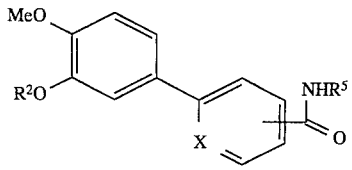

wherein X is CH or N and R$^2$ and R$^5$ are as defined above for formula I, the amide can only be in the para or meta position; and the compound of formula I cannot be trans-1-[4-[2-[3-(cyclopentyloxy)-4-methoxy-phenyl]-ethenylphenyl]-2-methyl-1H-imidazo[4,5-c]pyridine.

8. A method according to claim 7 wherein the inflammatory disease or condition is rheumatoid arthritis, osteoarthritis, asthma, bronchitis, chronic obstructive airways disease, psoriasis, allergic rhinitis, dermatitis or inflammatory bowel disease.

9. A pharmaceutical composition comprising a pharmaceutically acceptable diluent or carrier and a tumor necrosis factor inhibiting amount of a compound selected from the group consisting of compounds of the formula (I)

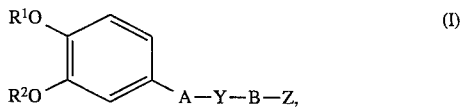

the racemic-diastereomeric mixtures and optical isomers of said compounds and the pharmaceutically acceptable salts thereof wherein R$^1$ is selected from the group consisting of methyl, ethyl, difluoromethyl and trifluoromethyl;

R$^2$ is selected from the group consisting of (C$_1$-C$_6$)alkyl, alkoxyalkyl having 3 to 7 carbons in the alkoxy portion and 2 to 4 carbons in the alkyl portion, phenoxyalkyl having 2 to 6 carbons in the alkyl portion, (C$_3$-C$_7$)cycloalkyl, (C$_6$-C$_9$)polycycloalkyl, phenylalkyl having 1 to 8 carbons in the alkyl portion, phenylaminoalkyl having 2 to 6 carbons in the alkyl portion and the amino may be optionally substituted with (C$_1$-C$_4$) alkyl and indanyl, where the alkyl portion of said alkyl, phenoxyalkyl, cycloalkyl, polycycloalkyl, phenylalkyl and indanyl may optionally be substituted with one or more fluorine atoms, —OH or (C$_1$-C$_4$)alkoxy, and the aryl portion of said phenylalkyl, phenoxyalkyl and indanyl may optionally be substituted with (C$_1$-C$_4$)alkyl, (C$_1$-C$_4$)alkoxy or halogen;

A and B are independently selected from the group consisting of a covalent bond, optionally substituted (C$_1$-C$_5$)alkylene, optionally substituted (C$_2$-C$_5$)alkenyl and optionally substituted phenylene, where said optionally substituted alkylene may be monosubstituted and each substituent is selected from the group consisting of oxo, (C$_1$-C$_4$)alkoxy, (CO$_2$R$^6$ and hydroxy, said optionally substituted alkenyl may be monosubstituted with (C$_1$-C$_4$)alkoxy or CO$_2$R$^6$, and said optionally substituted phenylene may be monosubstituted with (C$_1$-C$_4$)alkoxy, CO$_2$R$^6$ or hydroxy, wherein R$^6$ is hydrogen or (C$_1$-C$_4$)alkyl;

Y is selected from the group consisting of a covalent bond, O, NR$^6$ and S wherein R$^6$ is as defined above;

Z is selected from the group consisting of

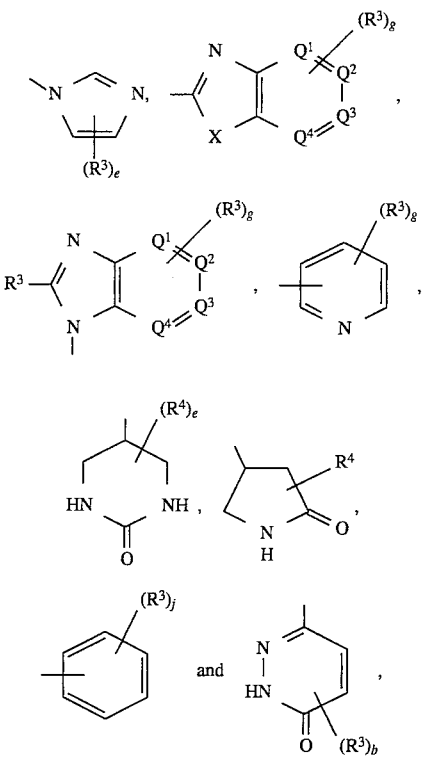

where Q$^1$, Q$^2$, Q$^3$, and Q$^4$ are independently N, CH or, when also bonded to B, C and provided that at least two of Q$^1$, Q$^2$, $Q^3$, and $Q^4$ are not N;

X is selected from the group consisting of $NR^4$ and S;

e is an integer from 1 to 3;

g is an integer from 1 to 4;

j is an integer from 1 to 5;

each $R^3$ is independently selected from the group consisting of hydrogen, halogen, $CF_3$, $(C_1-C_6)$alkyl, $CH(R^7)CO_2R^4$, $(C_1-C_6)$alkoxy, $CO_2R^4$, $CONR^4R^5$, CONHOH, $CH_2NR^4R^5$, $NR^4R^5$, nitro, hydroxy, CN, $SO_3H$, phenylalkyl having 1 to 4 carbons in the alkyl portion, $SO_2NR^4R^5$, $N(SO_2R^8)_2$ and $NHSO_2R^8$, where $R^4$ for each occurrence is independently selected from the group consisting of hydrogen, $(C_1-C_6)$alkyl, phenyl optionally substituted with $(C_1-C_4)$alkyl or halogen, $CH(R^7)CO_2R^6$, $(C_3-C_7)$cycloalkyl, phenylalkyl having 1 to 4 carbons in the alkyl portion and dialkylaminoalkyl having a total of 5 carbons in the dialkylamino portion and having 2 to 5 carbons in the alkyl portion where $R^6$ is as defined above, $R^5$ for each occurrence is independently selected from the group consisting of hydrogen, $(C_1-C_6)$alkyl, $(C_3-C_7)$cycloalkyl, phenylalkyl having 1 to 4 carbons in the alkyl portion, phenyl, pyridyl, pyrimidyl, thiazolyl and oxazolyl, or $R^4$ and $R^5$ are taken together with the nitrogen to which they are attached and form an optionally substituted saturated or unsaturated 5-or 6-membered ring, a saturated or unsaturated 6-membered heterocyclic ring containing two heteroatoms, or a quinoline ring optionally substituted with fluoro, where said optionally substituted saturated or unsaturated 5- or 6-membered ring may be mono-or di-substituted and each substituent is independently selected from the group consisting of alkyl having 1 to 4 carbons, $CO_2R^7$ wherein $R^7$ is as defined below, $CONH_2$, $CON(CH_3)_2$, oxo, hydroxy, $NH_2$ and $N(CH_3)_2$, and said saturated or unsaturated 6-membered heterocyclic ring containing two heteroatoms has the second heteroatom selected from the group consisting of O, S, NH, $NCH_3$, $NCOCH_3$ and $NCH_2Ph$;

$R^7$ for each occurrence is independently selected from the group consisting of hydrogen and $(C_1-C_4)$alkyl;

and $R^8$ is selected from the group consisting of $(C_1-C_6)$alkyl, $(C_3-C_7)$cycloalkyl, phenyl and phenylalkyl having 1 to 4 carbons in the alkyl portion;

with the proviso that:

when $R^1$ is methyl or ethyl; $R^2$ is $(C_7-C_9)$polycycloalkyl or indanyl; A, B and Y are covalent bonds; X is N; and $R^3$ is hydrogen;

then Z is not

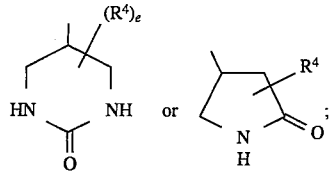

when the compound of formula I is

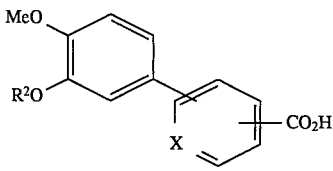

wherein X is CH or N and $R^2$ is as defined above for formula I, the $CO_2H$ can only be in the para position relative to the bond to the catechol moiety; when the compound of formula I is

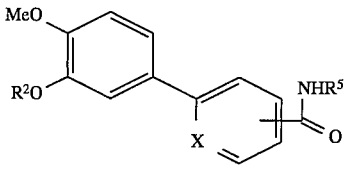

wherein X is CH or N and $R^2$ and $R^5$ are as defined above for formula I, the amide can only be in the para or meta position; and the compound of formula I cannot be trans-1-[4-[2-[3-(cyclopentyloxy)-4-methoxy-phenyl]-ethenylphenyl]-2-methyl-1H-imidazo[4,5-c]pyridine.

* * * * *